(12) United States Patent
Grady et al.

(10) Patent No.: US 10,789,706 B2
(45) Date of Patent: Sep. 29, 2020

(54) SYSTEMS AND METHODS FOR MEDICAL ACQUISITION PROCESSING AND MACHINE LEARNING FOR ANATOMICAL ASSESSMENT

(71) Applicant: HeartFlow, Inc., Redwood City, CA (US)

(72) Inventors: Leo Grady, Millbrae, CA (US); Michiel Schaap, Mountain View, CA (US); Edward Karl Hahn, III, San Carlos, CA (US)

(73) Assignee: HeartFlow, Inc., Redwood City, CA (US)

( * ) Notice: Subject to any disclaimer, the term of this patent is extended or adjusted under 35 U.S.C. 154(b) by 180 days.

(21) Appl. No.: 15/852,183

(22) Filed: Dec. 22, 2017

(65) Prior Publication Data

US 2018/0182096 A1  Jun. 28, 2018

Related U.S. Application Data

(60) Provisional application No. 62/438,509, filed on Dec. 23, 2016.

(51) Int. Cl.
*G06T 7/00* (2017.01)
*G16H 50/20* (2018.01)
(Continued)

(52) U.S. Cl.
CPC .......... *G06T 7/0012* (2013.01); *G06T 11/003* (2013.01); *G16H 10/60* (2018.01);
(Continued)

(58) Field of Classification Search
CPC . G06T 2207/30104; G06T 2207/30172; G06T 7/0012; G06T 2207/30004;
(Continued)

(56) References Cited

U.S. PATENT DOCUMENTS 10,628,943 B2 * 4/2020 Hsieh ................ G06N 3/08
2013/0121556 A1 * 5/2013 Matsumoto .......... A61B 6/50
382/132

(Continued)

FOREIGN PATENT DOCUMENTS

EP      2 784 749 A1   10/2014
WO   WO 2016/161356 A1  10/2016

*Primary Examiner* — Pinalben Patel
(74) *Attorney, Agent, or Firm* — Bookoff McAndrews, PLLC

(57) ABSTRACT

Systems and methods are disclosed for determining anatomy directly from raw medical acquisitions using a machine learning system. One method includes obtaining raw medical acquisition data from transmission and collection of energy and particles traveling through and originating from bodies of one or more individuals; obtaining a parameterized model associated with anatomy of each of the one or more individuals; determining one or more parameters for the parameterized model, wherein the parameters are associated with the raw medical acquisition data; training a machine learning system to predict one or more values for each of the determined parameters of the parametrized model, based on the raw medical acquisition data; acquiring a medical acquisition for a selected patient; and using the trained machine learning system to determine a parameter value for a patient-specific parameterized model of the patient.

20 Claims, 3 Drawing Sheets

(51) Int. Cl.
*G16H 30/40* (2018.01)
*G16H 50/50* (2018.01)
*G06T 11/00* (2006.01)
*G16H 10/60* (2018.01)
*G06N 20/00* (2019.01)

(52) U.S. Cl.
CPC ............ *G16H 30/40* (2018.01); *G16H 50/20* (2018.01); *G16H 50/50* (2018.01); *G06N 20/00* (2019.01); *G06T 2207/20081* (2013.01); *G06T 2207/30004* (2013.01); *G06T 2207/30104* (2013.01); *G06T 2207/30172* (2013.01)

(58) Field of Classification Search
CPC ........ G06T 11/003; G06T 2207/20081; G06N 20/00; G16H 50/20; G16H 10/60; G16H 50/50; G16H 30/40
See application file for complete search history.

(56) References Cited

U.S. PATENT DOCUMENTS

| | | | | |
|---|---|---|---|---|
| 2014/0241602 A1* | 8/2014 | Lynn | ...................... | G16H 50/70 382/128 |
| 2015/0038860 A1* | 2/2015 | Fonte | ........................ | A61B 6/50 600/505 |
| 2017/0132383 A1* | 5/2017 | Myers | ................... | G06F 3/0482 |
| 2018/0182096 A1* | 6/2018 | Grady | ..................... | G16H 50/50 |
| 2019/0122073 A1* | 4/2019 | Ozdemir | .............. | A61B 6/5217 |

* cited by examiner

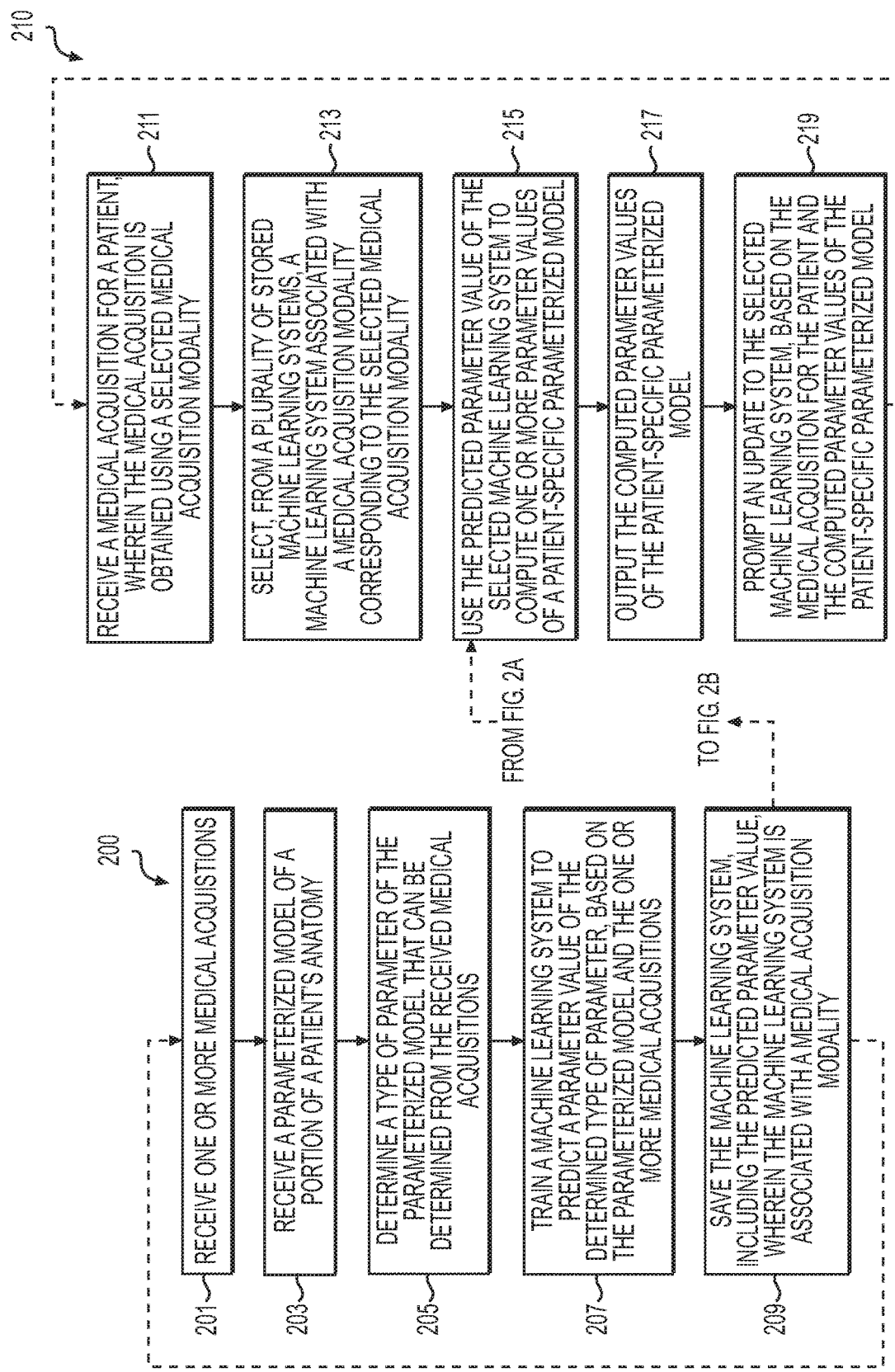

SYSTEMS AND METHODS FOR MEDICAL ACQUISITION PROCESSING AND MACHINE LEARNING FOR ANATOMICAL ASSESSMENT

RELATED APPLICATION

This application claims priority to U.S. Provisional Application No. 62/438,509 filed Dec. 23, 2016, the entire disclosure of which is hereby incorporated by reference in its entirety.

FIELD OF THE INVENTION

Various embodiments of the present disclosure relate generally to medical imaging and related methods. More specifically, particular embodiments of the present disclosure relate to systems and methods for determining anatomy from raw medical acquisition.

BACKGROUND

Medical imaging is a powerful clinical tool for assessing the health of a patient. Raw acquisition devices (e.g., computed tomography (CT), positron emission tomography (PET), single-photon emission computerized tomography (SPECT), angiography, magnetic resonance imaging (MRI), ultrasound, etc.) may collect a significant amount of data using the transmission and collection of energy and particles traveling through and originating from the patient (e.g., in the form of x-rays, positrons, photons, ultrasonic waves, magnetic fields, contrast agent, etc.). Often, acquired data is reconstructed into an image. The reconstructed image may be interpreted by a physician visually and/or using image analysis software to assess the patient anatomy or physiology.

However, information loss may occur during image reconstruction. For example, significant information loss may occur while transforming raw acquisition data to a set of discrete pixel intensity values. To account for this information loss, multiple different image reconstructions are often utilized to assist a physician in performing an accurate assessment of the patient (e.g., the use of a sharp and soft reconstruction kernel to assess, respectively, calcium and low density plaque on cardiac computed tomography angiograph (CTA) imaging). Unfortunately, any image reconstruction may still involve an information loss in transforming the raw acquisition to a set of images. Such information loss may result in a suboptimal assessment of patient health, or patient anatomy and physiology. Accordingly, a desire exists to assess the anatomy and physiology of a patient, without the information loss caused by the transformation of raw acquisition data to images.

SUMMARY

Systems and methods are disclosed for determining patient anatomy from machine learning of raw medical acquisition data from the patient. The disclosed systems and methods offer a way of assessing a patient's anatomy and physiology using raw data acquisitions versus image reconstructions. The presently disclosed systems and methods offer advantages in accuracy and processing speed over analysis of image reconstructions to assess a patient's anatomy and physiology. One such embodiment employs machine learning to predict measurements or parameters of a patient's anatomy and physiology. In one embodiment, disclosed machine learning systems and methods may involve two phases: first, a training phase in which a machine learning system is trained to predict anatomical parameters from raw acquisition data; and second, an application phase in which the machine learning system is used to produce predicted anatomical parameters for a specific patient, using only a the raw measurement data from a medical acquisition associated with the patient. Analogous machine learning systems may be trained and applied for various parameters in addition to anatomical parameters, e.g., physiological parameters, mechanical parameters, dynamic parameters, etc. Such embodiments are described in more detail at FIGS. 2A and 2B.

According to one embodiment, a method is disclosed for determining anatomy from raw medical acquisition data of a patient. The method includes obtaining raw medical acquisition data from transmission and collection of energy and particles traveling through and originating from bodies of one or more individuals; obtaining a parameterized model associated with anatomy of each of the one or more individuals; determining one or more parameters for the parameterized model, wherein the parameters are associated with the raw medical acquisition data; training a machine learning system to predict one or more values for each of the determined parameters of the parametrized model, based on the raw medical acquisition data; acquiring a medical acquisition for a selected patient; and using the trained machine learning system to determine a parameter value for a patient-specific parameterized model of the patient.

According to another embodiment, a system is disclosed for determining anatomy from a raw medical acquisition. The system includes a data storage device storing instructions for determining anatomy from raw medical acquisition data; and a processor configured to execute the instructions to perform a method including the steps of: obtaining raw medical acquisition data from transmission and collection of energy and particles traveling through and originating from bodies of one or more individuals; obtaining a parameterized model associated with anatomy of each of the one or more individuals; determining one or more parameters for the parameterized model, wherein the parameters are associated with the raw medical acquisition data; training a machine learning system to predict one or more values for each of the determined parameters of the parametrized model, based on the raw medical acquisition data; acquiring a medical acquisition for a selected patient; and using the trained machine learning system to determine a parameter value for a patient-specific parameterized model of the patient.

In accordance with yet another embodiment, a non-transitory computer readable medium for use on a computer system containing computer-executable programming instructions for a method of determining anatomy from raw medical acquisition data is provided. The method includes: obtaining raw medical acquisition data from transmission and collection of energy and particles traveling through and originating from bodies of one or more individuals; obtaining a parameterized model associated with anatomy of each of the one or more individuals; determining one or more parameters for the parameterized model, wherein the parameters are associated with the raw medical acquisition data; training a machine learning system to predict one or more values for each of the determined parameters of the parametrized model, based on the raw medical acquisition data; acquiring a medical acquisition for a selected patient; and using the trained machine learning system to determine a parameter value for a patient-specific parameterized model of the patient.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2A is an exemplary method for training a machine learning system to determine anatomy from raw medical acquisition data, according to an exemplary embodiment of the present disclosure.

FIG. 2B is an exemplary method for applying the trained machine learning system in order to determine anatomy from raw medical acquisition data, according to an exemplary embodiment of the present disclosure.

DESCRIPTION OF THE EMBODIMENTS

Figure 1A:
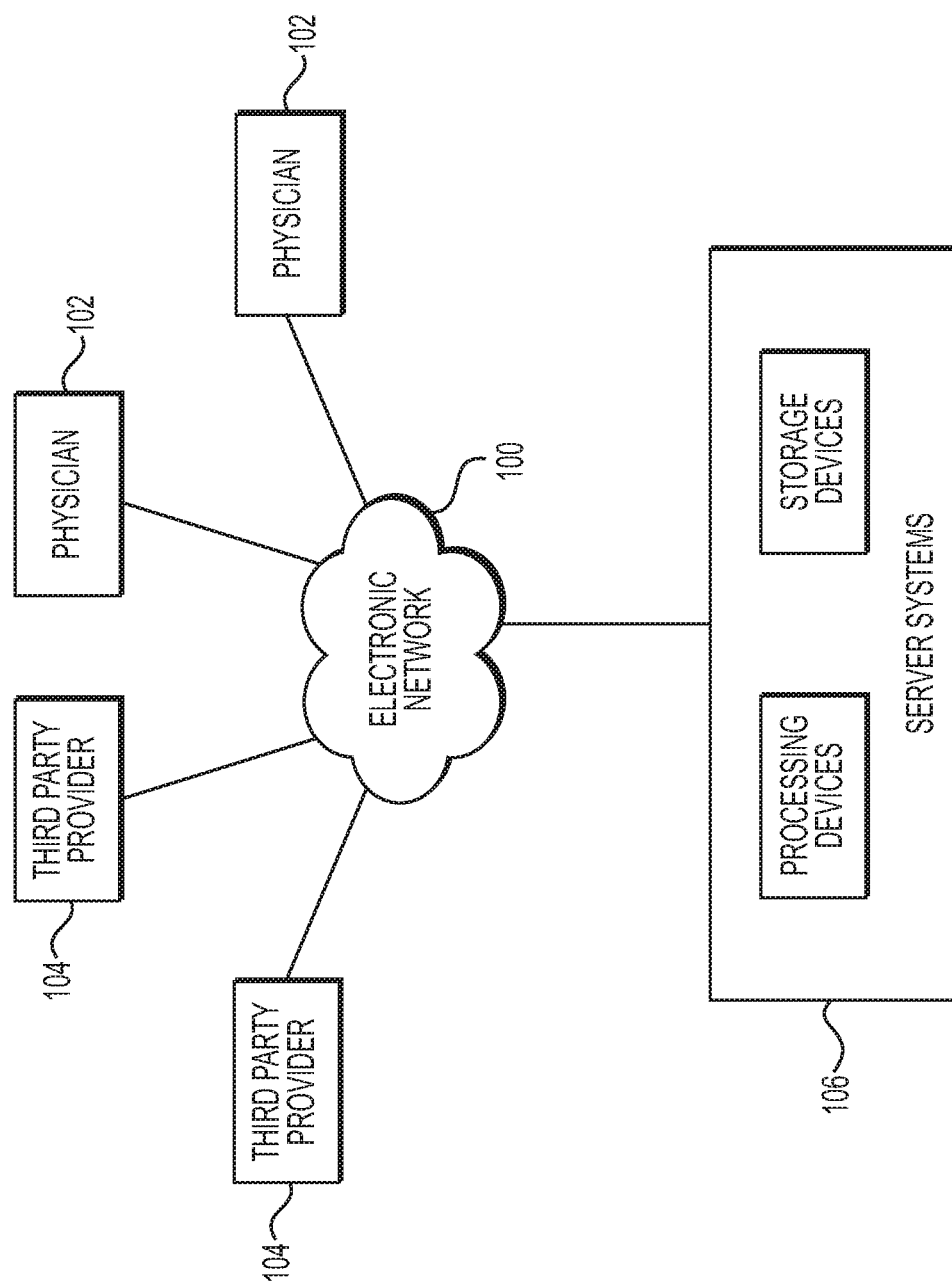
FIG. 1A is a block diagram of an exemplary system and network for determining anatomy from a medical acquisition, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts. As used herein, the term "exemplary" is used in the sense of "example," rather than "ideal."

As described above, raw patient data from medical acquisitions or images may be reconstructed to facilitate analysis or interpretation by physicians or image analysis software. However, information may be lost in the process of creating an image reconstruction from raw data. The present disclosure describes systems and methods of assessing patient anatomy and/or physiology using the raw acquisition data, rather than reconstructed images. In other words, the disclosed systems and methods may permit assessment of patient anatomy and/or physiology without creating an image intermediary from raw data. In this way, the assessments of patient anatomy and/or physiology may take advantage of the full capacity of acquired raw data, rather than performing assessments on reconstructed images comprised of acquired data that has undergone information loss. As described above, one exemplary system and method may include a training phase and an application phase (sometimes referred to as "production phase"). During the training phase, a machine learning system may be trained to predict patient-specific model parameter values. During the application phase, the trained model may be used to determine patient-specific model parameter value(s) from a patient acquisition.

The training phase may be executed in a number of ways. In one general form, the training phase may include receiving cases of raw acquisition data (e.g., k-space data from a T1-weighted magnetic resonance (MR) acquisition) and receiving expected output values associated with the raw acquisition data (e.g., the expected size or geometry of an individual's Hippocampus). The training phase may include training a machine learning system to learn the relation between the input (e.g., the raw acquisition data) and the output (e.g., parameter values describing the size/geometry of the hippocampus). The learned function "H" may be described as, Expected Output Value=$H$(raw acquisition data)

The training phase may also employ elements in addition to the machine learning system. These additional elements may simplify or facilitate the training of the machine learning system. For example, in one case, input may again include receiving expected output values associated with the raw acquisition data (e.g., the expected size or geometry of an individual's Hippocampus). However, the machine learning system training may be aided with an image analysis method, including knowledge of the relationship between raw acquisition data and a reconstructed image. The image analysis method may provide expected output values (e.g., parameter values describing the size/geometry of a hippocampus) when given the input of reconstructed images (from the raw acquisition data). Since the input in the present embodiment includes raw acquisition data rather than reconstructed images, the present embodiment may include simulating a reconstructed image from the raw acquisition data. The machine learning system may then be trained to find the relation between the simulated reconstructed image and the output (e.g., parameter values describing the size/geometry of the hippocampus). In this way, rather than the machine learning system having to learn the direct relation between raw acquisition data and anatomy (e.g., Expected Output Value=$H$(raw acquisition data)), the machine learning system may find the relationship between simulated reconstructed images and raw acquisition data, since the relation between reconstructed images and anatomy may be provided by the image analysis method. In other words, once the machine learning system understands the relation between simulated reconstructed images and the raw acquisition data, the output (e.g., parameter values describing the size/geometry of a hippocampus may be provided by the image analysis method. For example, the image analysis method may be referred to as method ("function S"), and finding a reconstruction method ("function R") to generate a reconstructed image from the raw acquisition data that may provide expected outputs may be described as, Expected Output Value=$S(R$(raw acquisition data))

This embodiment may facilitate the first, general embodiment in that the function H is broken into functions S and R, e.g., $H$(raw acquisition data)=$S(R$(raw acquisition data))

In addition, the machine learning training may be focused on learning function R, since function S may be provided as the image analysis method. In one embodiment, the reconstruction method R used for the simulated reconstructed image may be dictated by the expected outputs of the image analysis method, which may provide the relationship between reconstructed images and expected parameter values. For example, multiple reconstruction methods may be possible for a given set of raw acquisition data. The simulated reconstruction used for the machine learning system training may be chosen from the simulated reconstruction of raw acquisition data that most closely provides the expected output given by the image analysis method. For instance, generating the simulated reconstructed image for machine learning system training may include iteratively reconstructing the raw acquisition data either until the expected output associated with the simulated reconstruction matches the expected output of the image analysis method, or until no further improvement may be made to matching the expected output associated with the simulated reconstruction with the expected output of the image analysis method. No further improvement may mean that, after several iterations, multiple reconstructions generate expected output that is equally close to matching the expected output of the image analysis method. Each of the reconstructions may then be comparable for use as the simulated reconstruction of the machine learning system training.

Alternately or in addition, determining patient anatomy from raw medical acquisition data may involve prior information, e.g., information on data acquisition. The process may be executed absent or with minimal machine learning. For example, the input may again include receiving expected output values associated with the raw acquisition data (e.g., the expected size or geometry of an individual's Hippocampus). Further input may include knowledge of how an acquisition works, including the relation between model parameters and acquisition data. For instance, a system may understand that hippocampus of size x may correspond to a k-space measurement of y, simply due to knowledge of how acquisitions work, and not from anatomical data related to individuals or patients.

For the application phase in a process that does not necessarily entail prior anatomical data related to individuals or patients, one method may include iteratively modifying generic parametric model values until a simulated acquisition corresponding to a modified form of the generic parametric model corresponds to (or matches) the patients' raw medical acquisition data. For example, the method may include initiating a process for determining patient anatomy from raw medical acquisition data by starting with model parameters of an average individual, or model parameters based on some input associated with a patient (e.g., patient weight). Given the model parameters, acquisition data may be simulated from the prior knowledge of how acquisitions work. The model parameter values may be iteratively changed until the simulated acquisition data matches the actual measurement from a patient as well as possible (e.g., until no further improvement may be made to the match). In this case, the method may not include receiving prior anatomical data/expected outputs from individuals or patients. Rather, the method may focus on the relation between raw acquisitions and model parameter values.

Referring now to the figures, FIG. 1A depicts a block diagram of an exemplary system and network for determining anatomy from a medical acquisition. Specifically, FIG. 1A depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Sever systems 106 may also include processing devices for processing images and data stored in the storage devices. Alternatively or in addition, the present disclosure (or portions of the system and methods of the present disclosure) may be performed on a local processing device (e.g., a laptop), absent an external server or network.

Figure 1B:
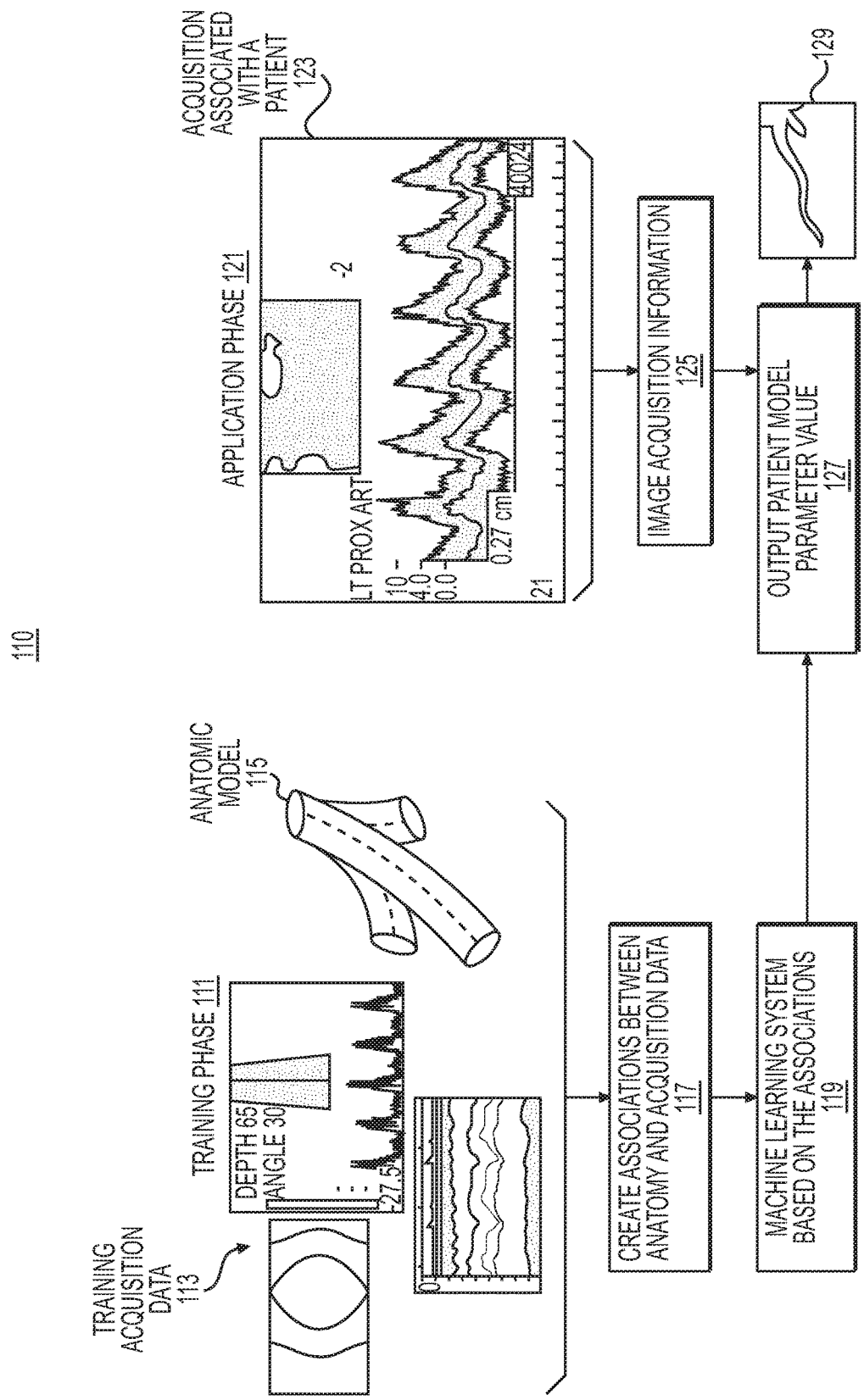
FIG. 1B is a block diagram of an exemplary overview of a training phase and an application phase for determining anatomy from raw medical acquisition data, according to an exemplary embodiment of the present disclosure.

FIG. 1B is a diagram of an overview 110 of an exemplary training phase 111 and an exemplary application phase 121 for determining anatomy from raw medical acquisition data, according to an exemplary embodiment of the present disclosure. In one embodiment, the training phase 111 may involve generating associations between model parameters and raw data from the acquisition (step 117). Exemplary model parameters may include vessel centerline, plaque location coordinates or composition, contrast agent concentration level, motion coordinates of an anatomical point, blood flow at a particular anatomical location, etc. The application phase 121 may then use the associations to determine medical data related to a given patient. For example, one embodiment of the application phase 121 may include using the associations to determine model parameter values for a given patient, when provided with raw data associated with the patient. In one embodiment, the model parameter values for a given patient may include a description or representation of the patient's anatomy. For example, the model parameter values may include a collection of labeled surfaces describing a boundary of an anatomical structure, boundaries between different anatomical structures, or a combination thereof. Alternately or in addition, one embodiment of the application phase 121 may include using the associations to determine a representation of the patient's anatomy comprising a discrete grid with an anatomical label for each grid point.

In one embodiment, the training phase 111 may include receiving image data (e.g., training acquisition data 113) and a parameterized model (e.g., anatomic model 115). Training acquisition data 113 may include raw data from any known medical imaging modality (e.g., CT, MR, SPECT, etc.). Training acquisition data 113 may further include any medical acquisition that may involve a graphic display (e.g., a sinogram of a CT system, echo measurements of receivers or Doppler measurements of receivers of an ultrasound device, electric field measurements from cardiac polarization wave imaging, measurements of wearable sensors, etc.). In one embodiment, parameterized anatomic model 115 may include 2-D, 3-D, or other geometric models of human anatomy. Alternately or in addition, parameterized anatomic model 115 may include parameterized models of physiology, composition, response, dynamics, etc., as described in detail in FIG. 2A. In other words, training acquisition data 113 may include clinical or medical data (e.g., image data) related to anatomical structures, function, or characteristics of parameterized model 115. Training acquisition data 113 may further be paired with anatomy/physiology/characteristics represented by parameterized anatomic model 115.

In one embodiment, the training acquisition data 113 and parameterized anatomic model 115 may be obtained from the same patient for whom patient-specific model parameter values are to be determined in an application phase. For example, one patient may have a machine learning system trained on his/her image/acquisition data. That machine learning system may be used to produce patient-specific model parameter values for the patient. Alternately or in addition, training acquisition data 113 and parameterized anatomic model 115 may be obtained from at least one individual, other than the patient. The data may be collected from a plurality of individuals, from literature, computed, simulated, etc. In such a case, the machine learning system trained on data of several individuals other than a patient may still be applied to patient image data in the application phase to predict patient-specific model parameter values. Other embodiments include using both patient data and individual data to train the machine learning system. For example, after an application phase, the patient image data of the application phase may be used as input to the training phase, to supplement the training of the machine learning system. That machine learning system may then be applied to predict patient-specific model parameters for another patient, or for the same patient at a different point in time.

In one embodiment, associations 117 may be created between the received training acquisition data 113 (e.g., image data) and the anatomy, physiology, and/or characteristics represented by parameterized anatomic model 115. For example, data acquisitions including echo measurements can provide information about a parameter involving the velocity of blood flow. As another example, a data acquisition including a sinogram of a CT system may provide information about geometric parameters of a portion of anatomy, or the presence of a geometric parameter related to anatomy (e.g., plaque). In one embodiment, a machine learning system 119 may store the associations 117 to predict future model parameter(s).

Machine learning system 119 may be used as an input to an exemplary application phase 121, where patient-specific parameter values may be determined. In one embodiment, application phase 121 may include obtaining a medical acquisition 123 of a patient of interest. One embodiment may also include obtaining image acquisition information 125 (e.g., image acquisition parameters) associated with medical acquisition 123. For example, a medical acquisition 123 including image data may be associated with image acquisition parameters 125. The image acquisition parameters may describe various imaging settings or patient physiological state(s) during the generation of the medical acquisition 123.

Machine learning system 119 may be applied to the received medical acquisition 123 (and acquisition information or parameter(s) 125) to determine a patient parameter value 127. In one embodiment, the patient parameter value 127 may include a parameter value of a model (e.g., an anatomical model, a motion model, a blood flow model, etc.). The application phase 121 may further include generating a display 129 including a representation of the model, or a representation based on the patient parameter value 127. The representation may include a surface model, graph, chart, color-coding, indicators, interactive displays, alerts, signals, or any known graphical objects. Various embodiments of graphical representations and displays are disclosed, for example, in U.S. Pat. No. 8,706,457 issued Apr. 22, 2014, entitled "Method and System for Providing Information from a Patient-Specific Model of Blood Flow," which is incorporated by reference in its entirety.

FIGS. 2A and 2B depict flowcharts of training and applying a machine learning system to determine anatomy from raw medical acquisition data. In particular, FIG. 2A is a flowchart of an exemplary method 200 of training a machine learning system to determine anatomy from images. FIG. 2B is a flowchart of an exemplary method 210 for using the trained machine learning system to predict the structure of a particular patient's anatomy. The methods of FIGS. 2A and 2B may be performed by server systems 106, based on information, images, and data received from physicians 102 and/or third party providers 104 over electronic network 100.

FIG. 2A is a flowchart of an exemplary method 200 for training a machine learning system to determine anatomy from raw medical acquisition data, according to an exemplary embodiment of the present disclosure. In one embodiment, step 201 may include receiving, using an electronic storage medium, one or more medical acquisitions of an individual or individuals. The medical acquisitions may include raw acquisition data based on transmission and collection of energy and particles traveling through and originating from the individuals' body (e.g., x-ray, positrons, photons, ultrasonic waves, magnetic fields, etc.). For example, one medical acquisition may be comprised of a k-space acquisition corresponding to an magnetic resonance signal and another medical acquisition may be comprised of a sinogram associated with x-ray beam attenuation. In one embodiment, the medical acquisition may include a sinogram of a CT system, a K-space acquisition of an MRI system, magnetic relaxation measurement(s) (e.g., by one or more coils of a parallel MRI system), echo measurement(s) of receivers (e.g., on an ultrasound device), Doppler measurement(s) of receivers (e.g., on an ultrasound device), electric field measurement(s) from an electric field imaging system (e.g., for cardiac polarization wave imaging), video(s) or photograph(s) of the individual's anatomy/physiology, data from wearable sensor(s) (e.g., including point, area, or volume measurement(s) of the sensors, time series acquisition(s) of any of the above, etc. In one embodiment, step 201 may further include receiving a set of acquisition parameters. Exemplary acquisition parameters include: timing and/or location of a contrast agent injection, X-ray dose information, Gantry speed, patient preparation (e.g., dosage and timing of beta blockers or nitrates), etc.

In one embodiment, step 203 may include receiving at least one parameterized model (mathematical, statistical, geometric, etc.) of at least part of the individual's or individuals' anatomy. Anatomy may include any structure of the individual's body, including vessel morphology, organ size and shape, vessel lumen geometry, etc. Other embodiments of step 203 may include (also or further) receiving at least one parametrized model of the individual's physiology, composition, response, or dynamics thereof. In one embodiment, models of physiology, composition, response, or dynamics may also be considered "anatomical models." Physiology may include any functions of the individual's body, including mechanical or biochemical functions of the individual and his/her organs. Composition may include a chemical make-up of the individual's anatomy or anatomical function, including plaque composition, blood viscosity, organ density, etc. Response may include the body's reaction to various stimuli, and dynamics may include measurements for density, composition, elasticity, concentration of a tracer or contrast agent, etc.

Examples of a parameterized model may include: a vascular model parameterized, for example, by vessel centerline location coordinates, where each centerline location may be additionally parameterized by a vessel radius and/or a blood pool density, a disease model parameterized by the location coordinates, volume, and/or density of calcified or low-density plaque, an organ and/or tissue model (e.g., a model of a patient's liver, kidney, spleen, brain, heart, bone, prostate, breast, lung, knee, fat, water, etc.) parameterized, for example, by the location coordinates of at least two surface points in which each surface point may be associated with a set of neighboring points (e.g., multiple times may be associated with different locations and/or neighbors for one or more surface points), a perfusion model in which the perfusion of blood or contrast agent may be parameterized as a concentration level, coordinate location, and/or time, a motion model that may associate vector of motion coordinates with one or more anatomical points, and/or a blood flow model that may associate a blood flow characteristic (e.g., pressure, velocity, etc.) with one or more location coordinates.

In one embodiment, step 205 may include determining a type of parameter of the parameterized model (of step 203) that can be determined from the medical acquisition (of step 201). For example, given a parameterized blood flow model, a medical acquisition of magnetic relaxation measurements may indicate a parameter value related to blood composition or the presence of a blood clot. In such a case, blood composition may be a parameter "type," and presence of blood clot may be another parameter value "type." As another example, given an anatomical motion model, a medical acquisition of Doppler measurements may indicate a value related to tissue motion or velocity. As such, additional exemplary parameter types may include "tissue motion" or "velocity." Step 205 may include discerning types of parameter values related to the parametrized model (of step 203) that may be ascertained or estimated from the medical acquisition (of step 201).

In one embodiment, step 207 may include using a computational device (e.g., computer, laptop, DSP, smart phone, tablet, GPU, etc.) to train a machine learning system to predict model parameter(s) values of the determined type of parameter, based on the parameterized model and the one or more medical acquisitions. For example, if the determined parameter type (e.g., from step 205) is "tissue velocity," step 207 may include determining a value of tissue velocity in centimeters per second, given a certain Doppler measurement input from an ultrasound device. As another example, if the determined parameter type is "presence of a blood clot," the machine learning system may be trained to predict "yes" or "no," based on various magnetic relaxation measurements by a parallel MRI system. In yet another example, if the determined parameter type is a value of thickness of the left ventricle myocardium, step 207 include determining the value of thickness directly from a cardiac CT sinogram. Further, if the determined parameter type is a value indicating the size of a hippocampus, step 207 may include determining the value directly from the k-space measurement of a T1-weighed brain MRI scan. [

In one embodiment, method 200 may include receiving a plurality of medical acquisitions and training the machine learning system using the plurality of acquisitions (step 207). The plurality of medical acquisitions may be obtained from one individual, a group of individuals within a single demographic (e.g., a defined patient population, hospital, age group, geographical region, etc.), or a patient of interest at a given point of time. Acquisitions used to train the machine learning system may comprise a "training set." Multiple machine learning techniques may be used for this training. Exemplary machine learning techniques for training the model parameter machine learning system include: estimating the conditional probabilities and prior probability for a Bayesian method, random forests, k-nearest neighbors, k-means, backpropagation, deep learning, multilayer perceptrons, logistic regression, linear regression, manifold learning techniques (e.g., locally linear embedding, isomap, etc.), semi-supervised learning techniques (e.g., if training acquisitions are available without corresponding patient models), etc. For example, given a parameterized model of tumor growth and a plurality of longitudinal (long term) time-series k-space acquisitions of patient tumor progression, a random forest may be trained to regress tumor size. Alternately or in addition, the training may employ methods that may not involve machine learning. For example, given a parameterized cardiac motion model and a plurality of CT sinograms with associated values for cardiac motion model parameters, a convolutional neural network may be trained via backpropagation to minimize a loss function describing the difference between predicted model parameter values and parameter values of a given model.

In one embodiment, step 209 may include storing results of the machine learning system including predicted parameter value(s). In one embodiment, a machine learning system may be adapted for each type of medical acquisition obtained. For example, each acquisition modality may have a designated machine learning system, e.g., a system for CT data, a system for Doppler measurements, a system for angiography data, and a system for wearable sensor data, etc. In another embodiment, acquisitions may be categorized by type. For instance, one machine learning system may be trained on acquisitions of anatomy (e.g., CT scans, angiography data, volume measurements, etc.), while another machine learning system may be trained on acquisitions of physiology (e.g., blood flow or blood pressure measurements, perfusion data, wearable sensor data, etc.). In yet another embodiment, a single machine learning system may provide predictions of parametric model parameters for any medical acquisition.

FIG. 2B is a flowchart of an exemplary method 210 for training a machine learning system to determine anatomy from raw medical acquisition data, according to an exemplary embodiment of the present disclosure. The method of FIG. 2B may be performed by server systems 106, based on information received from physicians 102 and/or third party providers 104 over electronic network 100.

In one embodiment, step 211 may include receiving a medical acquisition of a patient. In one embodiment, the patient may be a person other than the individual or group of individuals. Alternately or in addition, the medical acquisition may be obtained from the patient at a point of time later than any patient medical acquisitions used for the training set.

In one embodiment, step 213 may include selecting a machine learning system associated with the type of medical acquisition of the patient medical acquisition. For example, if step 211 includes receiving a CT scan, step 213 may include selecting a machine learning system trained using, at least in part, CT acquisition data. In an alternate embodiment, the medical acquisition of the patient may be obtained, depending on the machine learning systems available. For example, if a machine learning system based on CT acquisition data is available, a health care professional may elect to acquire a CT scan for a patient. In another instance, an angiography machine learning system may be available, but trained on less data than the CT scan machine learning system. In such a case, the health care professional may still opt for acquiring the CT scan, since the CT machine learning system may be more reliable than the angiography machine learning system.

In one embodiment, step 215 may include using a computational device (e.g., computer, laptop, DSP, smart phone, tablet, GPU, etc.), to determine a set of parameter values for a patient-specific model using the trained machine learning system (e.g., of method 200). In other words, step 215 may include generating or computing a patient-specific model, using a trained machine learning system. In one embodiment, step 215 may include determining one or more patient-specific model parameter values based on the machine learning system (of method 200) and the received patient medical acquisition (of step 211). Alternately or in addition, step 215 may include determining acquisition parameter(s) associated with the received medical acquisition of step 211 and projecting the input acquisition parameter(s) to a learned manifold of a machine learning system of method 200 in order to compute patient-specific model parameter values. In yet another embodiment, step 215 may include using Bayes' rule to calculate an estimated probability distribution of a patient-specific model parameter value using the machine learning system of method 200 and the patient medical acquisition of step 211. In such an embodiment, step 215 may further include selecting a set from the probability distribution (e.g., using maximum likelihood or maximum a posteriori). For example, if many training examples (e.g., sets of acquisition and target values) are available, one could choose to use a machine learning method with many degrees of freedom, for example an artificial neural network. If only a few training examples are available, step 215 may employ more traditional methods, e.g., support vector machines.

Step 215 of generating or computing the patient-specific model may be supplemented with prior information on how raw acquisition data measurements may correlate to the anatomy or physiology of the patient. (e.g. prior information or raw data acquisition priors associated with CT physics may indicate how anatomical information relates to the measured acquisition data). For example, a reconstructed image of the raw medical acquisition of the patient may be used as additional input for the machine learning system (alongside the raw data). As another example, step 215 may include learning how to reconstruct an image from the medical acquisition of the patient, such that the reconstruction may be optimal for a predefined image analysis technique that may provide model parameter value(s) of the patient. In one embodiment, step 217 may include outputting the determined patient-specific model parameter values to an electronic storage device. One output may include, for example, a display including a representation of patient anatomy or physiology based on the determined patient-specific model parameter values. Another exemplary output may include determining one or more additional properties of a patient anatomy and/or physiology using the determined patient-specific model parameter values. Additional properties may include, for example, organ/tissue volume, organ/tissue shape, vessel cross-sectional size and/or shape, organ/tissue surface area and/or shape, stenosis size, tumor/lesion presence or absence, tumor/lesion location, ejection fraction, stroke volume, a blood flow characteristic, plaque burden, calcium score, plaque vulnerability, tissue viability, myocardial wall motion, nuchal translucency, presence or absence of patient pathology, valvular regurgitation, and/or patient diagnosis.

In one embodiment, step 219 may further include prompting an update to the stored machine learning system based on the received patient medical acquisition (e.g., of step 211), the determined patient-specific model parameter values, and/or input on the determined patient-specific model parameters. Input on the determined patient-specific model parameters may include user feedback on the patient-specific model parameter values, including selection, verification, or modification of the values.

In a further embodiment, output patient-specific model parameter value(s) (e.g., of step 217) may be compared to parameter(s) of reconstructions based on the raw medical acquisition data. For example, image reconstruction(s) may be generated based on the raw medical acquisition data. In some cases, the image reconstruction(s) may include rectilinear reconstructions. Anatomic models may also be generated based on the image reconstruction(s). In one embodiment, patient-specific model parameter value(s) generated directly from the raw medical acquisition data may be compared to image reconstruction(s) generated from the raw medical acquisition data, or compared to anatomic model(s) generated from the image reconstruction(s). The comparison may be used to generate confidence metrics in the image reconstruction(s) or anatomic model(s) generated from the image reconstruction(s). For example, the image reconstruction(s) or anatomic model(s) generated from the image reconstructions may be validated based on determined patient-specific model parameter value(s) (e.g., of step 217). One embodiment may include selecting an image reconstruction or anatomic model of a patient, based on determined patient-specific model parameter value(s) and using the image reconstruction or anatomic model for diagnostic analyses (e.g., blood flow modeling/simulations, plaque rupture predictions, perfusion estimates, etc.). Various embodiments of diagnostic analyses using image reconstructions and anatomic models are disclosed, for example, in U.S. Pat. No. 8,315,812 issued Nov. 20, 2012, entitled "Method and System for Patient-Specific Modeling of Blood Flow," which is incorporated by reference in its entirety.

The presently disclosed systems and methods offer advantages over analysis of image reconstructions to assess a patient's anatomy and physiology, in that the full capacity of acquired raw data may be used for the assessments. Resulting assessments are less impacted by potential errors or data loss introduced by image reconstruction. The disclosed systems and methods provide machine learning embodiments as a way to assess a patient's anatomy and physiology from raw data acquisitions. In particular, the disclosed systems and methods use machine learning to predict measurements or parameters of a patient's anatomy and physiology.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining anatomy from raw medical acquisition data, the method comprising:
obtaining raw medical acquisition data from transmission and collection of energy and particles traveling through and originating from bodies of one or more individuals;
obtaining a respective parameterized model associated with anatomy of each individual of the one or more individuals;
determining, for the respective parameterized model of each individual, one or more parameters from or associated with the raw medical acquisition data;
training a machine learning system, using the raw medical acquisition data and the respective parameterized model of each individual, to predict one or more values for one or more parameters in a given parameterized model based on given raw medical data;

acquiring a medical acquisition for a selected patient, the medical acquisition comprising data from transmission and collection of energy and particles traveling through and originating from the selected patient's body; and using the trained machine learning system and the acquired medical acquisition for the selected patient to determine at least one parameter value for a patient-specific parameterized model of the selected patient.

2. The method of claim 1, wherein the determined at least one parameter value includes an anatomical feature measurement comprising a vessel centerline, an anatomical point, an anatomical surface point or boundary, or a combination thereof, and wherein the respective parametrized model includes a vascular model, a disease model, a perfusion model, a motion model, a blood flow model, or a combination thereof.

3. The method of claim 1, further comprising:
generating an image reconstruction based on the medical acquisition for the selected patient; and
validating the image reconstruction based on the determined parameter value.

4. The method of claim 1, further comprising:
determining an association between the raw medical acquisition data and the one or more parameters of the respective parametrized model; and
predicting the one or more values for each of the one or more parameters of the patient-specific parametrized model based on the determined association.

5. The method of claim 1, further comprising:
determining a set of acquisition parameters associated with the raw medical acquisition data; and
training the machine learning system based on the set of acquisition parameters.

6. The method of claim 1, further comprising:
determining a data acquisition modality associated with the machine learning system; and
acquiring the raw medical acquisition data for the selected patient based on the data acquisition modality associated with the machine learning system.

7. The method of claim 1, wherein the medical acquisition includes sinogram or k-space data obtained from one or more individuals other than the selected patient, data obtained from the selected patient, or simulated data.

8. The method of claim 1, wherein the at least one parameter value for the patient-specific parameterized model is determined without creating an image intermediary from the raw medical acquisition data.

9. A system for determining anatomy from raw medical acquisition data, the system comprising:
at least one data storage device storing instructions for determining anatomy from raw medical acquisition data; and
at least one processor configured to execute the instructions to perform a method including:
obtaining raw medical acquisition data from transmission and collection of energy and particles traveling through and originating from bodies of one or more individuals;
obtaining a respective parameterized model associated with anatomy of each of the one or more individuals;
determining, for the respective parameterized model of each individual, one or more parameters associated with the raw medical acquisition data;
training a machine learning system, using the raw medical acquisition data and the respective parameterized model of each individual, to predict one or more values for one or more parameters in a given parameterized model based on given raw medical data;
acquiring a medical acquisition for a selected patient, the medical acquisition comprising data from transmission and collection of energy and particles traveling through and originating from the selected patient's body; and
using the trained machine learning system and the acquired medical acquisition for the selected patient to determine at least one parameter value for a patient-specific parameterized model of the selected patient.

10. The system of claim 9, wherein:
The at least one determined parameter value includes an anatomical feature measurement comprising a vessel centerline, an anatomical point, an anatomical surface point or boundary, or a combination thereof, and
the respective parametrized model includes a vascular model, a disease model, a perfusion model, a motion model, a blood flow model, or a combination thereof.

11. The system of claim 10, wherein the method further includes:
determining an association between the raw medical acquisition data and the one or more parameters of the respective parametrized model; and
predicting the one or more values for each of the one or more parameters of the patient-specific parametrized model based on the determined association.

12. The system of claim 9, wherein the method further includes:
generating an image reconstruction based on the medical acquisition for the selected patient; and
validating the image reconstruction based on the at least one determined parameter value.

13. The system of claim 9, wherein the method further includes:
determining a set of acquisition parameters associated with the raw medical acquisition data; and
training the machine learning system based on the set of acquisition parameters.

14. The system of claim 9, wherein the method further includes:
determining a data acquisition modality associated with the machine learning system; and
acquiring the raw medical acquisition data for the selected patient based on the data acquisition modality associated with the machine learning system.

15. The system of claim 9, wherein the medical acquisition includes sinogram or k-space data obtained from one or more individuals other than the selected patient, data obtained from the selected patient, or simulated data.

16. The system of claim 9, wherein the at least one parameter value for the patient-specific parameterized model is determined without creating an image intermediary from the raw medical acquisition data.

17. A non-transitory computer readable medium for use on a computer system containing computer-executable programming instructions for performing a method of determining anatomy from raw medical acquisition data, the method comprising:
obtaining raw medical acquisition data from transmission and collection of energy and particles traveling through and originating from bodies of one or more individuals;

obtaining a respective parameterized model associated with anatomy of each of the one or more individuals;

determining, for the respective parameterized model of each individual, one or more parameters associated with the raw medical acquisition data;

training a machine learning system, using the raw medical acquisition data and the respective parameterize model of each individual, to predict one or more values for one or more parameters in a given parameterized model based on given raw medical data;

acquiring a medical acquisition for a selected patient, the medical acquisition comprising data from transmission and collection of energy and particles traveling through and originating from the selected patient's body; and using the trained machine learning system and the acquired medical acquisition for the selected patient to determine at least one parameter value for a patient-specific parameterized model of the selected patient.

18. The non-transitory computer readable medium of claim 17, wherein the at least one determined parameter value includes an anatomical feature measurement comprising a vessel centerline, an anatomical point, an anatomical surface point or boundary, or a combination thereof, and wherein the respective parametrized model includes a vascular model, a disease model, a perfusion model, a motion model, a blood flow model, or a combination thereof.

19. The non-transitory computer readable medium of claim 17, the method further comprising:

generating an image reconstruction based on the medical acquisition for the selected patient; and validating the image reconstruction based on the determined parameter value.

20. The non-transitory computer readable medium of claim 17, the method further comprising:

determining an association between the raw medical acquisition data and the one or more parameters of the respective parametrized model; and predicting the one or more values for each of the one or more parameters of the patient-specific parametrized model based on the determined association.

\* \* \* \* \*